United States Patent [19]
Reif

[11] Patent Number: 5,479,921
[45] Date of Patent: Jan. 2, 1996

[54] ENDOTRACHEAL TUBE STABILIZER

[76] Inventor: Jeanne B. Reif, 1499 A NW. Amherst Dr., Port St. Lucie, Fla. 34986

[21] Appl. No.: 191,465

[22] Filed: Feb. 4, 1994

Related U.S. Application Data

[63] Continuation of Ser. No. 900,690, Jun. 17, 1992, Pat. No. Des. 347,686.

[51] Int. Cl.⁶ ................................................ A61M 16/00
[52] U.S. Cl. ............................... 128/207.17; 128/DIG. 26
[58] Field of Search ...................... 128/207.17, DIG. 26, 128/200.28, 206.27; 2/422

[56] References Cited

U.S. PATENT DOCUMENTS

| | | | |
|---|---|---|---|
| 3,055,371 | 9/1962 | Kulick | 604/100 |
| 3,108,282 | 10/1963 | Rehman et al. | 2/422 |
| 3,234,939 | 2/1966 | Morton, Jr. | 128/206.27 |
| 4,191,180 | 3/1980 | Colley et al. | 128/DIG. 26 |
| 4,457,461 | 7/1984 | Docking et al. | 2/422 |
| 4,766,610 | 8/1988 | Mattes | 2/422 |
| 4,867,154 | 9/1989 | Potter et al. | 128/DIG. 26 |
| 5,009,227 | 4/1991 | Nieuwstad | 128/DIG. 26 |
| 5,069,206 | 12/1991 | Crosbie | 128/DIG. 26 |
| 5,269,296 | 12/1993 | Landis | 128/DIG. 26 |

FOREIGN PATENT DOCUMENTS

| | | | |
|---|---|---|---|
| 300002 | 8/1932 | Italy | 128/200.28 |

Primary Examiner—Aaron J. Lewis
Attorney, Agent, or Firm—Albert H. Reuther

[57] ABSTRACT

The endotracheal tube stabilizer device consists of a head frame with three projections and a separate endotracheal tube clamping/securing device. The endotracheal tube stabilizer device is arranged structurally in a configuration such that an endotracheal tube can be securely positioned while allowing for freedom of movement of the patient and support of the ventilatory tubing. The three pronged head frame is composed of a hardened, yet flexible material which is padded, and is able to be sprung aside to allow for the insertion of the patients head, securing it in a firm, yet cradling manner. The superior-central projection of the head frame is positioned over the top medial aspect of the head. A left projection and a right projection, arising from the posterior aspect of the central projection, respectively are positioned over the left and right sides of the head towards the cheek area at an approximately 90 degree angle respectively being located in a predetermined angular configuration relative to the superior-central projection. The top of the superior-central projection of the head frame contains a device for securing the ventilatory tubing.

19 Claims, 3 Drawing Sheets

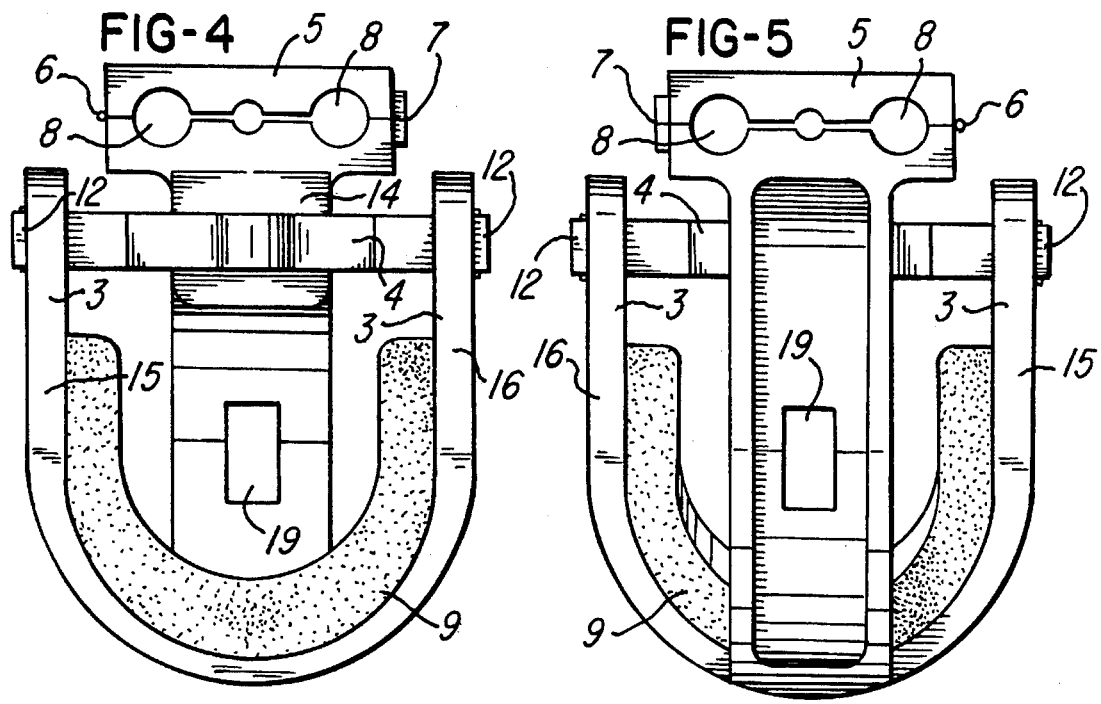
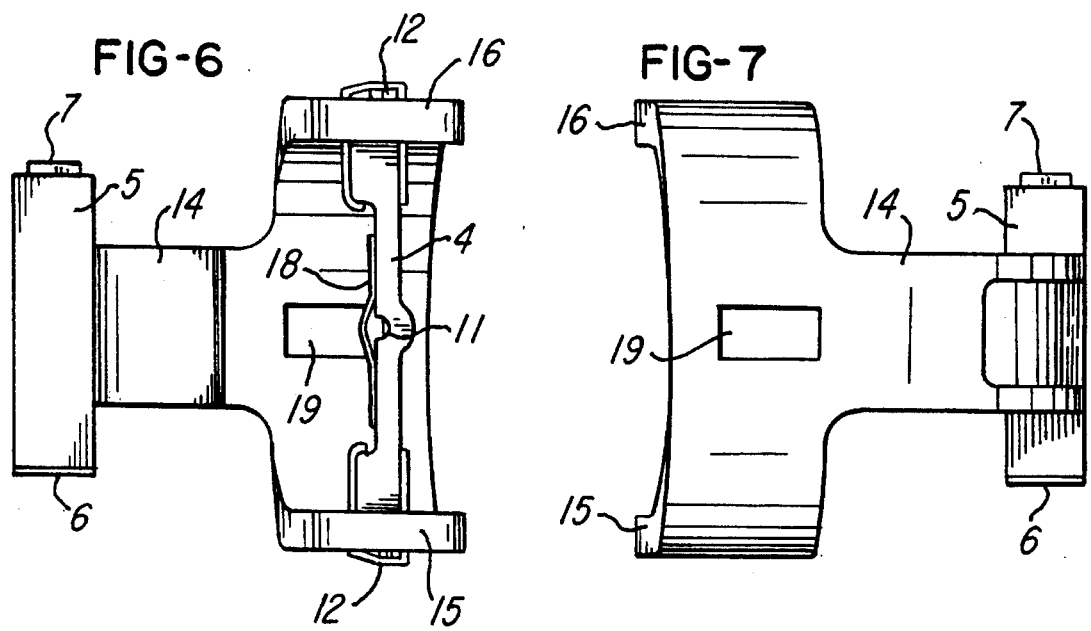

ENDOTRACHEAL TUBE STABILIZER

This is a continuation application of allowed Design Ser. No. 900,690 of Jeanne Brock Reif filed Jun. 17, 1992, now U.S. Pat. No. 347,686-Reif issued Jun. 7, 1994, pertaining to an ENDOTRACHEAL TUBE STABILIZER for use on neonates/children/adults with all materials being hypoallergenic and including respiratory apparatus support fixture components fitted with an endotracheal tube support bar positioned transversely as to ends of a substantially U-shaped frame structure that has curved side arms of moderately resilient plastic-like material capable of limited flexure but having relatively firm clamping strength; the structure has a configuration that may be sprung aside for insertion of the patient's head against an interior plastic-foam replaceable pad surface contoured to support and restrain the endotracheal tube relative to the patient's head; the head can move and windows for access to feel neonate suture lines as to head inter-cranial pressure are provided as required with the curved side arms adjoining a flexible endotracheal tube held by tape, Velcro or even mechanical clamp means in a centrally indented portion of the support bar as to tubing in clamped position between complementary portions of an apparatus clamp hinged at one end and at an opposite end latched in closed relationship to hold the tubing on the central elbow portion of the frame angularly in spaced relationship to the endotracheal tube projecting from an end of a tubular coupling laterally of which the tubing for waste gas exhaust, instrumentation and oxygen supply extends in a configuration having features thereof as disclosed herewith.

BACKGROUND OF THE INVENTION

Field of the Invention

At times during the course of medical care, an endotracheal tube is inserted into the mouth and downward into the trachea of a patient. The external portion of the endotracheal tube is then connected to a ventilator by way of ventilatory tubing. The ventilator respectively ventilatory means then pumps prescribed amounts of oxygenated air through the ventilatory tubing and endotracheal tube, into the patients lungs. This process assists and/or takes the place of breathing for the patient.

The placement and securement of the endotracheal tube is extremely important for ensuring the delivery of oxygenated air into the lungs. In adults, the proximal portion of the endotracheal tube is typically fitted with a small balloon, which when inflated, helps to prevent shifting or movement of the endotracheal tube and seals the trachea. The distal portion of the endotracheal tube is then typically secured to the face of the patient by means of adhesive tape.

In neonates and children, the endotracheal tube does not have a balloon component, due to the narrowing of the trachea in common for this age group. This makes securement of the endotracheal tube extremely important and difficult. The most popular methods for securing an endotracheal tube in these patients typically employ the use of a clamp-like device locked around the endotracheal tube near the mouth and/or large amounts of adhesive tape applied to the endotracheal tube and face of the patient. However, the prior art of securing the endotracheal tube has many problems, among them:

a) Taping of the endotracheal tube requires accurate skilled placement and necessitates the maintenance of this placement throughout the use of the endotracheal tube. The process of performing the taping procedure can employ extraneous movements which may alter placement of the tube, thereby compromising ventilatory effectiveness;

b) The presence of saliva, an enzymatic fluid, can encourage irritation of the skin and/or promote the dissolution of adhesive chemicals, resulting in movement and alteration of tube position;

c) The ability to inspect and/or provide care to the mouth is severely limited due to the presence of tape extending from the endotracheal tube towards the face of the patient;

d) In neonates, the use of a clamp-like device can result in the pinching of the lip area, which typically followed by application of tape, is hidden from view and detection. The discovery of this action may not occur until the patient develops a severe infection and/or sepsis, and can result in permanent disfigurement of the facial area;

e) Any repositioning of the endotracheal tube requires the removal and reapplication of tape which can alter placement and irritate the facial area, especially in case of long term intubation which is not unusual in neonates.

DESCRIPTION OF THE PRIOR ART

Currently available endotracheal tube stabilizing devices demonstrate deficiencies in many major areas. Such devices as those shown in U.S. Pat. No. 4,774,946-Ackerman et al dated Oct. 4, 1988, U.S. Pat. No. 4,821,736-Watson dated Apr. 18, 1989, and U.S. Pat. No. 4,622,034-Shattuck dated Nov. 11, 1986 employ the use of elastic straps around the patients head. This method is unsuitable as it may impede circulation and cause tissue damage, and is undesirable on neonates whose head size can change rapidly. Other devices such as U.S. Pat. No. 4,548,200-Wapner dated Oct. 22, 1985 and U.S. Pat. No. 4,520,813-Young dated Jun. 4, 1985 while utilizing non-elastic straps, are prone to slip in place thereby altering the position of the tube and compromising ventilatory effectiveness. Devices, such as those shown in U.S. Pat No. 4,867,154-Potter et al dated Sep. 19, 1989, involve the application of tape to the patients face. This can cause irritation to the skin and can loosen over time, also resulting in alteration of tube position and ineffective ventilation.

Another major deficiency in the prior art of endotracheal tube securing devices is the lack of support and/or securement of the ventilatory tubing. During the course of nursing care the ventilation tubing distal to the endotracheal tube is commonly manipulated in a manner which creates a tendency for the endotracheal tube to move also. In addition to this, the ventilatory tubing, by its presence and weight, can pull upon the endotracheal tube thereby altering its position within the trachea. To limit this effect movement of the patient's body is typically restricted and limited, so as not to contribute to pulling upon the endotracheal tube. Unfortunately, prolonged positioning of the body in one place can result in discomfort, and/or breakdown of the skin. The previously mentioned devices and devices such as disclosed by U.S. Pat. No. 4,744,358-McGinnis dated May 17, 1988 do not address the problem of support or securement of the ventilatory tubing, nor the issue of restricted movement.

Other problems with the prior art of endotracheal tubing stabilizing devices is the lack of a quick and easy way to apply the device to the patient. Complicated devices requiring the use of more than one person in handling or applying the device is not advantageous in an acute care setting. Also, as typically in the case of neonates, the endotracheal tube may need to be repositioned as the neonates grows in size. The prior art of endotracheal tube stabilizers can be taken to demonstrate an inability of these devices to be quickly repositioned and secured, and may involve the tedious reapplication of tape or elastic devices which take time and can further traumatize the skin.

SUMMARY OF THE INVENTION

The general purpose and object of the present invention is to provide an endotracheal tube stabilizing device which alleviates the above and other problems inherent in securing and maintaining the positioning of an endotracheal tube, while allowing for ease of placement and use, and movement of the patient without compromising ventilatory effectiveness.

The present invention is composed of an open head frame with ventilatory tubing securing capability, and a endotracheal tube support bar. The head frame is suitably padded by way of a supportive material in a contoured shape, which is medical quality plastic foam such as polyurethane, for example. A significant feature of this invention is that the application of this padding and the design of the head frame ensures secure placement of the head frame around the cranium, in such a manner, as to prevent the head frame from shifting position while not causing injury, impeding blood flow, or necessitating the attachment of tape to the patient's body.

In addition, another significant aspect and feature of the present invention is the use of a method to secure the ventilatory tubing to the superior aspect of the head frame not addressed in the prior art. This feature secures to the head frame, and supports the ventilatory tubing in such a manner as to: insure the coordinated movement of the ventilatory tubing with the head frame and patient, and eliminate the effect of pulling on the endotracheal tube by the ventilatory tubing. These capabilities will thereby reduce the effect of pulling upon the endotracheal tube by the ventilatory tubing, reduce the possibility of alteration of the endotracheal tube position, and allow for greater freedom of movement and positioning of the patient's body without effecting tube position.

Another significant feature of the present invention is that the head frame, via structural configuration, also incorporates cut-out portions over the superior-central, left, and right side projections which allow for the visualization of the head surface, and provide a place for the attachment of the endotracheal tube support bar, in a secure manner and within a variety of positions, as necessitated for the individualized optimal placement of the endotracheal tube.

The present invention also contemplates in one aspect thereof of an endotracheal support bar which is constructed of, but not limited to, a hard yet slightly flexible lightweight plastic material such as polycarbonate or high density polyethylene which is more costly to use. This support bar is attached to and/or closed around the endotracheal tube, and then attached to the left and right side projections of the head frame, in a secure manner, utilizing, but not limited to a restraining type of material such as Velcro, and/or the like fastening means present on the support bar and the internal aspects of the left and right side projections of the head frame, such as locking serrations.

In order to secure the endotracheal tube to the support bar, a significant feature of the endotracheal support bar is the presence of a centrally located cylindrical opening which corresponds to the diameter of the endotracheal tube. The sides of this cylindrical opening contain a adhesive material in one preferred embodiment, similar but not limited to, a Velcro material which adheres to, a similar component applied to the outer circumference of the endotracheal tube, thereby securing the endotracheal tube to the support bar. Another significant feature of the support bar is the presence of restraining capabilities, similar to, but not limited to locking serrations to the left and right side of the central cylindrical opening, extending out towards the ends of the support bar, which further locks the support bar in a closed position around the endotracheal tube, further securing the endotracheal tube to the support bar.

Another significant feature of the invention is that each end of the support bar is designed to secure the support bar to the left and right side projections of the head frame in the optimal anatomical position for the patient, and maintain that position, via structural configuration thereof and/or but not limited to, the use of materials with restraining-like properties. Another significant feature of the invention is that the support bar can also be quickly and easily unfastened from the head frame to allow for repositioning of the endotracheal tube within the trachea, and then quickly and securely refastened to the head frame in its new position. This feature takes into account the need to respond swiftly to the rapidly changeable and potentially life threatening situations commonly associated with acutely ill patients.

In summary, all of the above significant features of this invention can be provided to eliminate the need for tape and/or a clamp-like device directly over the mouth area, thereby reducing the possibility of irritation, alteration in positioning, infection, or disfigurement as mentioned previously as limitation of prior art and/or in a) through e). And most significantly, this present invention addresses the need to eliminate the effect of pulling upon the endotracheal tube by the ventilatory tubing, by the incorporation of a ventilatory tubing support device on the superior projection of the head frame, thereby improving patient care, maximizing comfort, and increasing safety.

These objects and other objects and advantages of the present invention will appear more clearly from the following specification in conjunction with the accompanying drawings, in which like reference numerals designate like parts throughout the figures thereof.

BRIEF DESCRIPTION OF THE DRAWINGS

FIG. 4 is a front elevational view of the frame structure in FIG. 1;

FIG. 5 is a rear elevational view of the frame structure;

FIG. 6 is a top plan view of the frame structure;

FIG. 7 is a bottom plan view of the frame structure;

DESCRIPTION OF PREFERRED EMBODIMENTS

Figure 1:
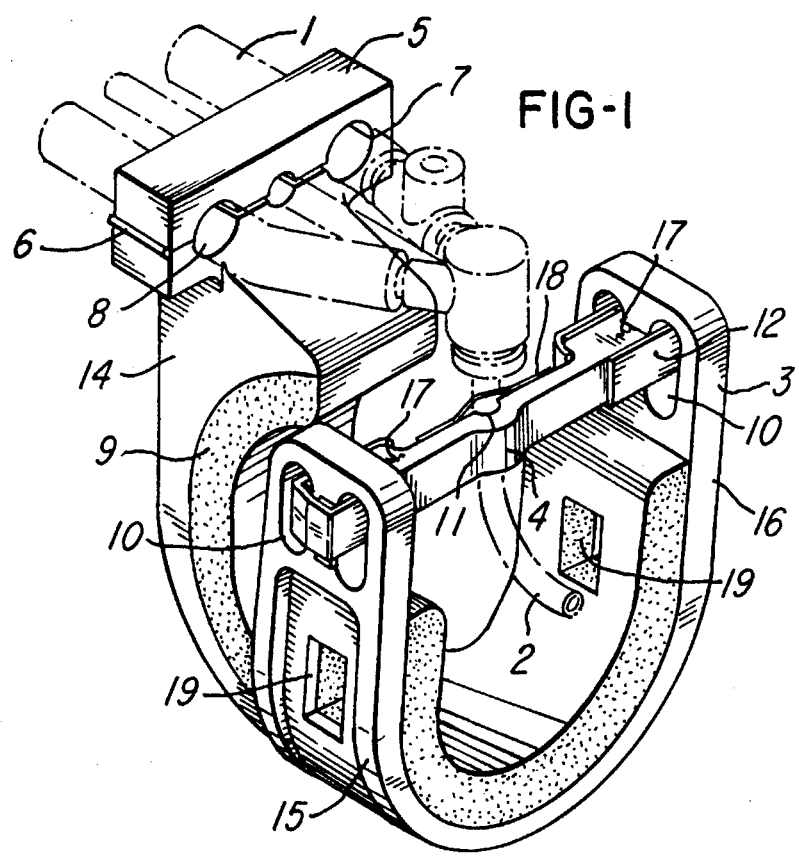
FIG. 1 is a perspective view of the endotracheal tube stabilizer arrangement showing respiratory assist apparatus tubing (ventilatory tubing) with a coupling in a juncture location and illustrating top, front, and one side of the frame structure thereof to show features in accordance with the present invention.

FIG. 1 is a view that collectively depicts the endotracheal tube stabilizing device with the ventilatory tubing 1 and endotracheal tube 2 shown in phantom. The endotracheal tube stabilizing device consists of a head frame 3 and an endotracheal tube support bar 4. The superior projection of the head frame has a ventilatory tubing securing device 5 which has a hinged structural configuration 6 on, but not limited to the right side and a clamping mechanism 7 on, but not limited to the left side. The ventilatory tubing 1 is placed inside the opened ventilatory securing device 5 and is held in position by means of cylindrical depressions 8. The ventilatory securing device is then closed, locking the ventilatory tubing in place. The head frame 3 also contains an interior contoured supportive padding 9 and openings 10 and windows 19 on the superior, left, and right projections.

The endotracheal tube support bar 4 is shown in position relative to the head frame 3 and the endotracheal tube 2 in phantom. The support bar contains a central cylindrical opening 11 which surrounds the endotracheal tube 2. This cylindrical opening 11 has materials capable of adhesive qualities similar, but not limited to Velcro type material 18, which is not shown in further detail, to assist in the attachment/securing of the support bar 4 to the endotracheal tube 2. The support bar 4 is also capable of being locked around the endotracheal tube and attached to the left and right projections of the head frame by means of, but not limited to restraining capabilities of securing means 12 and locking serrations 17 which are not illustrated in further detail, and present in the support bar and the internal aspects of the openings 10 of the left and right projections of the head frame.

Figures 2, 3:
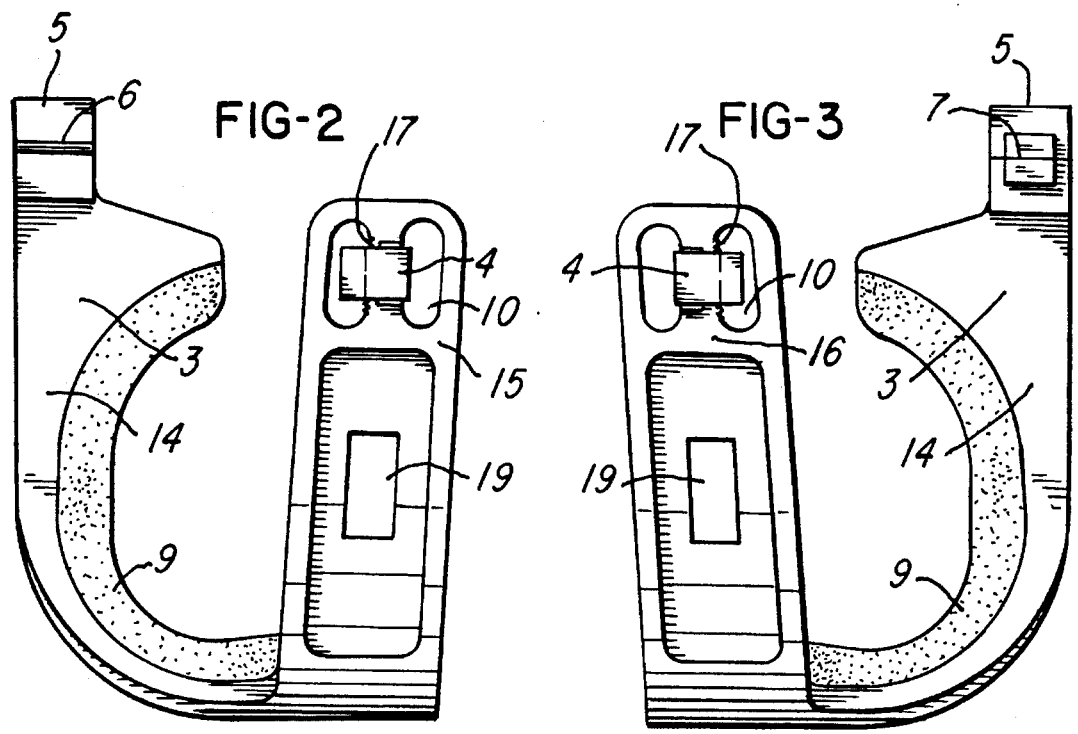
FIG. 2 is a right side elevational view of the head frame structure including the hinged clamp on the central elbow portion angularly to one side of a side arm fitted securely with the interior plastic-foam pad adhering thereto and having a surface contoured to support a patient's head, and moreover, one possible embodiment of a serrated design is illustrated on the interior of the opening of the side projection, fastening it to the support bar.
FIG. 3 is a left side elevational view of the structure of FIG. 2 including a latched clamp on the central elbow portion angularly to one side of an opposite side arm fitted with the interior plastic-foam pad.

FIG. 2 is a view that shows a right side view of the endotracheal tube stabilizing device consisting of a head frame 3 with interior contoured supportive padding 9 and an endotracheal tube support bar 4. The superior projection of the head frame 14 has a ventilatory tubing securing device 5 with a hinged structural configuration 6 on, but not limited to the right side.

The endotracheal tube support bar 4 is shown in position and attached to the head frame through the openings 10 of the right side projection 15 by means of, and not limited to, one possible embodiment of a locking serrated capability of securing means 17. One possible variation of the placement of windows 19 on the right side projection for examination is shown, but not limited to this position, nor just this projection of, the head frame.

FIG. 3 is a left side view of the endotracheal tube stabilizing device consisting of a head frame 3 with interior contoured supportive padding 9, which is made of medical quality plastic foam such as polyurethane, for example, and an endotracheal tube support bar 4, which is made of polycarbonate material and like material having qualities similar to the polycarbonate material. The superior projection of the head frame 14 has a ventilatory tubing securing device 5 with a clamping mechanism 7 on, but not limited to the left side.

The endotracheal tube support bar 4 is shown in position and attached to the head frame through the openings 10 of the left side projection 16 by means of, and not limited to, one possible embodiment of a locking serrated capability of securing means 17. One possible variation of the placement of windows 19 on the left side projection for examination is shown, but not limited to this position, nor just this projection of, the head frame.

FIGS. 4, 5, 6 and 7 show the frame structure 3 per se in front, rear, top and plan views to facilitate recognition of the features thereof identified by reference numeral designations approximately corresponding to those in other views of the drawings.

Figure 8:
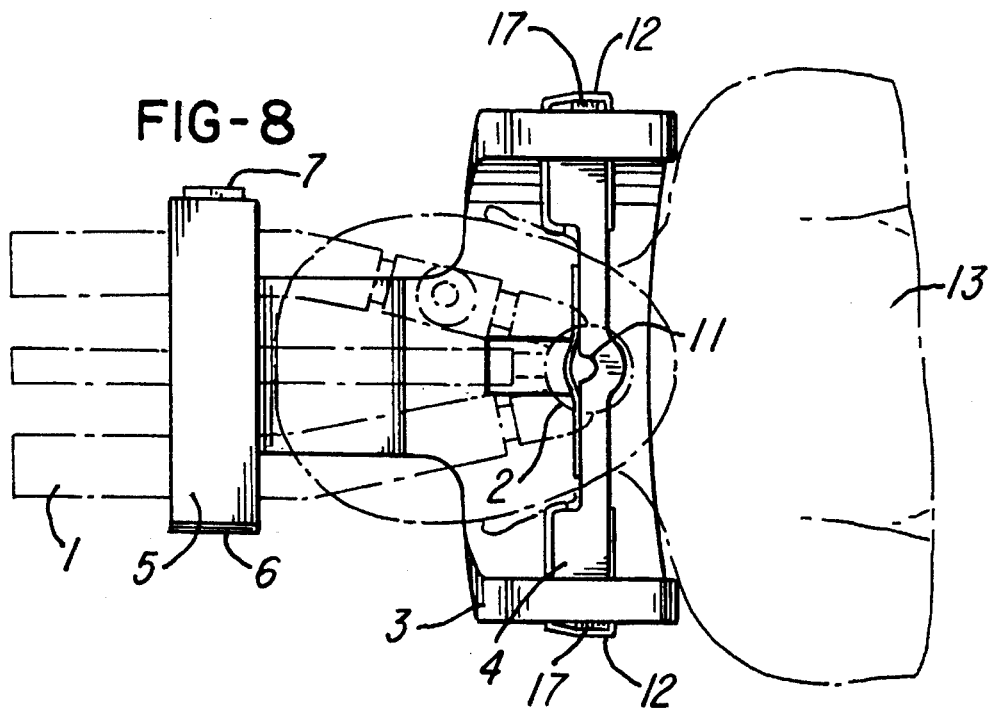
FIG. 8 is a top plan view showing the frame structure with side arms bridged by the tracheal tube support bar and with the elbow portion clamp for the respiratory assist apparatus tubing in phantom applied to a patient also in phantom.

FIG. 8 is a top plan view of features of the invention with the patient 13, ventilation tubing 1 and endotracheal tube 2 shown in phantom. The head frame 3, ventilation tubing securing device 5 with hinging means 6 and clamping 7 mechanism, and endotracheal tube support bar 4 thereof shown in position respective to the patient 13. One possible embodiment of the central cylindrical opening 11 is depicted with the presence of an adhesive material similar to, but not limited to a Velcro type of material 18. Also present on the support bar are one possible embodiment of possible locations of restraining capabilities of securing means 12 and locking serrations 17 present within but not limited to the head frame side projections and the support bar.

Figure 9:
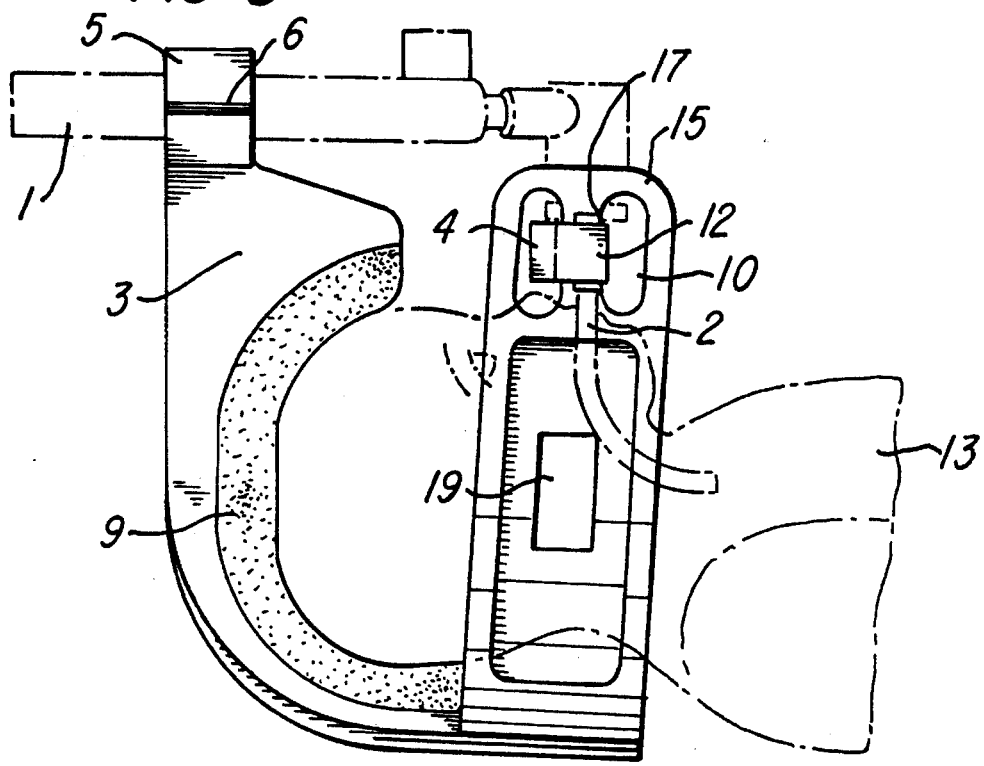
FIG. 9 is a right side elevational view also showing in phantom the respiratory assist apparatus as applied to a patient.

FIG. 9 is a right view of features of the invention with the patient 13 and ventilatory tubing 1 and endotracheal tube 2 shown in phantom. The head frame 3 and the interior contoured padding 9 is shown in place relative to the patients head. The ventilatory tubing securing device 5 and hinge structural configuration 6 thereof are shown in the closed position around the ventilatory tubing 1. The right side aspect of the endotracheal tube support bar 4 is depicted attached through the opening 10 of the right side projection 15 of the head frame by means of restraining capabilities 12 and/or but not limited to locking serration means 17 which are not illustrated fully in further detail. One possible variation of the placement of windows 19 on the right side projection for examination is shown, but not limited to this position, nor just this projection of the head frame.

Mode of Operation

In a medical setting, the patient 13 is first intubated by the insertion of an endotracheal tube 2 into the patients trachea, as shown in FIG. 9, and correct placement and positioning of the endotracheal tube is checked. The endotracheal tube stabilizing configuration of this present invention which consists of the head frame 3 and the endotracheal tube support bar 4 as shown in FIG. 1 is then utilized.

The superior 14, right 15 and left 16 projections of the head frame as shown in FIG. 1, are pushed out to accommodate the insertion of the head of the patient, with the facial area facing up between the projections. Once the head is inserted, the padded projection of the head frame springs back towards the facial area, to form a fitted and secure envelopment around the head, in a manner that along with the contour padding 9, hinders movement or slippage of the head frame over the cranium.

In one preferred embodiment, as shown in FIG. 1, an adhesive component similar to, but not limited to, a Velcro material 18 is then placed around the outer circumference of the endotracheal tube. This adhesive component 18 mates with the adhesive component already present within the central cylindrical opening of the endotracheal tube support bar 11. The endotracheal tube support bar 4 is then positioned around the outer circumference of the endotracheal tube, attaching the endotracheal tube 2 to the support bar 4 in a secure manner by means of, but not limited to, adhesive components similar to a Velcro material 18.

Once the endotracheal tube is secured to the support bar, the two ends of the support bar are then placed through the openings 10 on the head frame located on the left and right side projections as shown in FIG. 1. Restraining capabilities of securing means 12, and/or adhesive components similar to but not limited to a Velcro material 18, and/or locking serrations 17 are located on the internal surfaces of the left and right side projections of the head frame and the support bar. After insertion of the ends of the support bar into the openings in the left and right projections of the head frame, the restraining capabilities of securing means, Velcro material, and/or locking serrations are employed, attaching and locking the support bar to the head frame in a secure manner.

Once the attachment of the support bar to the head frame has been completed, the ventilatory tubing securing device 5 on the superior projection of the head frame is then opened up to accommodate the placement of the ventilation tubing 1 within cylindrical depressions 8 thereof, and then closed in a locked manner, as shown in FIG. 1, securing the ventilation tubing within the securing device. The patient can now be moved or repositioned without altering the positioning of the endotracheal tube.

One possible variation of the location of windows 19 present on the head frame is shown in FIG. 1. These windows can be utilized during the usage of the endotracheal tube stabilizing device for examination of the ears, fontanels, and/or other needed areas on the head of the patient, and are not limited to the exact placement depicted.

At times during the usage of an endotracheal tube it may become necessary to alter the positioning of the endotracheal tube 2 within the patient to maximize ventilatory effectiveness. While using the endotracheal tube stabilizing device, the changing of endotracheal tube positions can be accomplished quickly, easily, and safely by unfastening the restraining materials 12, adhesive type components 18, and/or unlocking the locking serrations 17 at each end of the endotracheal support bar 4 as shown in FIG. 1, and reattaching the support bar in its new position within the openings 10 of the right side projection 15 and left side projection 16 of the head frame. The ventilatory tubing securing device 5 is then opened and the ventilatory tubing 1 is repositioned to coincide with the new positioning of the endotracheal tube 2 so that no pulling is present upon the endotracheal tube by the ventilatory tubing. Once the ventilatory tubing is in correct position, the ventilator 7 tubing securing device 5 is then locked as shown in FIG. 1, securing the placement.

The support bar 4 as shown in FIG. 1, as a modification thereof in one alternative embodiment, is further secured around the endotracheal tube 2 by means of, but not limited to restraining capabilities of securing means 12 and/or locking serrations 17, distal to the central cylindrical opening 11 and mouth area, further securing the endotracheal tube 2 to the endotracheal tube support bar 4 in such a manner as to prevent any alteration of position of the endotracheal tube in relation to the support bar.

Another modification of the features of the present invention in a further alternative embodiment is the structural configuration of the internal contoured padding 9 of the head frame which is present but not limited to structure of the head frame. The contoured padding in this modification is allowed to depart from the structure of the head frame in such a manner as to cross over the cranium, adjoining other areas of padding and/or the head frame over the cranium, in order to stabilize positioning of the head frame over the cranium in a secure manner.

Another modification of the features of the present invention in a further alternative embodiment is the presence of additional side projections over the superior, left and right aspects of the cranium in such a manner and structural configuration as to further ensure the stability and positioning of the head frame on the cranium of the patient in a secure manner.

The left and right projections, arising from the posterior aspect of the central projection, respectively are positioned over the left and right sides of the head towards the cheek area at an approximately 90 degree angle, respectively being located in a predetermined angular configuration relative to the superior-central projection; the side projections are not limited to a substantially 90 degree angle configuration from the superior-central projection.

The broken line showing of the endotracheal tubing and the person in FIGS. 8 and 9 is for illustrative purposes only and forms no part of the claimed invention.

The present invention is, of course, in no way restricted to the specific disclosure of the specification and drawings, but also encompasses any modifications within the scope of the appended claims.

What I claim is:

1. An endotracheal tube stabilizer, comprising:
   a head frame including at least three projections arranged structurally in a configuration as a three-pronged head frame composed of a hardened, yet flexible material;
   padded means provided in predetermined locations on the three-pronged frame which is capable to be sprung aside to allow for insertion of a patient's head secured in a firm yet cradling manner to receive an endotracheal tube; and
   a separate endotracheal tube clamping-securing device including an endotracheal tube support bar arranged structurally to be fastened to and located around the endotracheal tube, said three-pronged head frame including a superior-central projection thereof positioned over a top medial aspect of the patient's head as well as a left projection and a right projection respectively arising from a posterior aspect of said central projection.

2. An endotracheal tube stabilizer according to claim 1, in which said left projection and said right projection respectively are positioned over the left and right sides of the patient's head towards a cheek area of the head at an approximately 90 degree angle to said superior-central projection.

3. An endotracheal tube stabilizer according to claim 1, in which a top portion of said superior-central projection of the head frame contains a device for securing ventilatory tubing, and said left and right projections of the head frame contain cut-away areas for insertion and fastening of the endotracheal tube support bar.

4. An endotracheal tube stabilizer according to claim 3, in which said device for securing ventilatory tubing includes a hinge means located at one end thereof and that allows movement to access cylindrical depressions of the device in complementary closed relationship.

5. An endotracheal tube stabilizer according to claim 4, in which the ventilatory tubing includes portions for waste gas exhaust, instrumentation and oxygen supply.

6. An endotracheal tube stabilizer according to claim 4, in which said device for securing ventilatory tubing at an opposite location remote from said hinge means includes an end latch means in closed relationship to hold the ventilatory tubing on said central projection of said frame angularly in spaced relationship to the endotracheal tube projecting from an end of a tubular coupling laterally of which tubing for waste gas exhaust, instrumentation and oxygen supply extends in a predetermined configuration.

7. An endotracheal tube stabilizer according to claim 1, in which said endotracheal tube support bar is composed of a hardened yet flexible material with a central circular opening, said support bar being arranged structurally to be fastened to and located around an endotracheal tube.

8. An endotracheal tube stabilizer according to claim 7, in which said fastened relationship of said support bar relative to said endotracheal tube exists via an adhesive material.

9. An endotracheal tube stabilizer according to claim 8, in which said adhesive material is a Velcro material.

10. An endotracheal tube stabilizer according to claim 1, in which said endotracheal support bar is structurally provided with fastening-restraining means on each end of the bar, which enables attachment thereof in a secure manner to said left and right projections of the head frame, thereby anchoring said endotracheal support bar to said head frames.

11. An endotracheal tube stabilizer according to claim 1, in which said padded means of said left and right projections has a substantially U-shaped configuration, and window means are provided at diagonally opposite locations through said padded means as well as said left and right projections, said window means being provided for access to feel neonate suture lines as to head inter-cranial pressure.

12. An endotracheal tube stabilizer according to claim 11, in which said window means can be utilized during usage of the endotracheal tube stabilizer for examination of ears, fontanels as well as other areas on the head of the patient.

13. An endotracheal tube stabilizer according to claim 11, in which said window means are provided over superior-central, as well as left and right side projections, said side projections being located in a predetermined angular configuration from the superior-central projection.

14. An endotracheal tube stabilizer according to claim 11, in which said head frame via structural configuration also incorporates cut-out portions over superior-central, left and right side projections which allow for visualization of a head surface, and provide a place for attachment of the endotracheal tube support bar, in a secure manner and within a variety of positions, as necessitated for individualized optimal placement of the endotracheal tube.

15. An endotracheal tube stabilizer according to claim 11, in which said head frame also contains an interior contoured supportive padding as well as openings and windows on superior-central, left and right projections.

16. An endotracheal tube stabilizer according to claim 1, in which said padded means is contoured to allow departure from structure of the head frame in such a manner as to cross over the cranium, adjoining other areas of padding respectively the head frame,over the cranium, in order to stabilize positioning of the head frame over the cranium in a secure manner.

17. An endotracheal tube stabilizer according to claim 1, in which securing means including locking serrations are provided, lateral to a central cylindrical opening and mouth area, further securing the endotracheal tube to the endotracheal tube support bar in such a manner as to prevent any alteration of position of the endotracheal tube in relation to the support bar.

18. An endotracheal tube stabilizer according to claim 1, in which said padded means is a medical quality plastic foam.

19. An endotracheal tube stabilizer according to claim 1, in which said support bar is constructed of polycarbonate material.

* * * * *